(12) United States Patent
Shanbrom

(10) Patent No.: US 7,297,716 B2
(45) Date of Patent: *Nov. 20, 2007

(54) ENHANCED PRODUCTION OF BLOOD COMPONENTS, BLOOD CELLS AND PLASMA WITHOUT FREEZING

(75) Inventor: Edward Shanbrom, Santa Ana, CA (US)

(73) Assignee: Shanbrom Technologies, LLC, Ojai, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/280,501

(22) Filed: Oct. 25, 2002

(65) Prior Publication Data

US 2003/0129167 A1  Jul. 10, 2003

Related U.S. Application Data

(63) Continuation-in-part of application No. PCT/US02/03996, filed on Feb. 7, 2002, which is a continuation-in-part of application No. 09/694,178, filed on Oct. 23, 2000, now Pat. No. 6,881,731, and a continuation-in-part of application No. 09/778,681, filed on Feb. 7, 2001, now Pat. No. 6,541,518.

(60) Provisional application No. 60/278,496, filed on Mar. 23, 2001.

(51) Int. Cl.
*A61K 47/00* (2006.01)
*A01N 25/00* (2006.01)

(52) U.S. Cl. ........ 514/784; 514/785

(58) Field of Classification Search ........ 424/667; 514/784
See application file for complete search history.

(56) References Cited

U.S. PATENT DOCUMENTS

| | | |
|---|---|---|
| 3,560,475 A | 2/1971 | Fekete et al. |
| 3,631,018 A | 12/1971 | Shanbrom |
| 3,682,881 A | 8/1972 | Fekete et al. |
| 3,803,115 A | 4/1974 | Fekete et al. ........ 260/112 B |
| 4,069,219 A | 1/1978 | Weier |
| 4,086,218 A | 4/1978 | Shanbrom ........ 260/112 B |
| 4,305,871 A | 12/1981 | Shanbrom ........ 260/112 B |
| 4,327,086 A | 4/1982 | Fukushima et al. ........ 424/117 |
| 4,925,665 A | 5/1990 | Murphy ........ 424/532 |
| 4,977,246 A | 12/1990 | Lee et al. ........ 530/383 |
| 5,196,428 A | 3/1993 | Meanwell ........ 514/253 |
| 5,770,704 A | 6/1998 | Godowski |
| 6,037,116 A | 3/2000 | Wiggins et al. ........ 435/1.1 |
| 6,403,381 B1 * | 6/2002 | Mann et al. ........ 436/69 |

FOREIGN PATENT DOCUMENTS

| | | |
|---|---|---|
| DE | 3316464 | * 11/1984 |
| EP | 0 272 551 A2 | 6/1998 |
| WO | WO 93/04678 | 3/1993 |
| WO | WO 93/21933 | 11/1993 |
| WO | WO 96/18292 | 6/1996 |

OTHER PUBLICATIONS

Oldurova, Problemy Gematol., i Perelivan. Krovi., 1961, 6 No. 11, 52-5.*
J.L. Veron, et al., *Combined Cohn/chromatography purification process for the manufacturing of high purity human albumin from plasma*, 1993, pp. 183-188.
K. Pedersen, *Inhibition of bacterial haemolysis on blood agar medium by oxalate or citrate used as anticoagulants*, 1973, pp. 384.
D. Thompson, et al., *Fibrin Glue: A review of its preparation, efficacy, and adverse effects as a tropical hemostat*, 1988, pp. 946-952.
S. Arrighi, et al., *Process for the isolation of highly purified factors IX, X and II from prothrombin complex or human plasma*, 1995, pp. 183-188 (abstract).

* cited by examiner

*Primary Examiner*—Alton Pryor
(74) *Attorney, Agent, or Firm*—Venable, LLP

(57) ABSTRACT

The blood collection, processing and transfer by separation of discrete components containing additional citrate (at least about trisodium citrate 2% w/v) in one or other of collection or processing bag provides for enhanced yield and purity of cryoprecipitate. Inhibiting the activation or denaturation of blood components including blood cells and plasma proteins and with the removal of the activated and denatured components thereby improving safety and efficacy of end products, which include fibrin glue, is achieved. In addition, the process allows "cryo" precipitate to be prepared at temperatures above freezing and without freezing the plasma.

24 Claims, 2 Drawing Sheets

ENHANCED PRODUCTION OF BLOOD COMPONENTS, BLOOD CELLS AND PLASMA WITHOUT FREEZING

RELATED APPLICATIONS

The present application is a continuation-in-part of and claims priority from International Patent Application No. PCT/US02/03996 filed Feb. 7, 2002, designating the United States, which in turn was continuation in part of U.S. patent application Ser. No. 09/694,178 filed Oct. 23, 2000, now U.S. Pat. No. 6,881,731 and U.S. patent application Ser. No. 09/778,681 filed on 7 Feb. 2001 now U.S. Pat. No. 6,541,518 and U.S. patent application Ser. No. 60/278,496 filed 23 Mar. 2001. To the extent allowable, all these applications are incorporated by reference herein.

BACKGROUND OF THE INVENTION

1. Area of the Art

The present invention relates to an improved method for producing increased amounts of safe coagulation factor concentrates from blood plasma.

The invention is also directed to enhancing the yield and purity of blood components and inhibiting the activation or denaturation of certain blood components, blood cells and plasma proteins, and to the removal of activated and denatured components, thereby improving the safety and efficacy of end products.

2. Description of the Prior Art

There are a number of medical indications for administration of "clotting" or "coagulation" factors from human blood. These factors are proteins that cause the clotting of blood to staunch bleeding from wounds, etc. Individuals with any of a series of genetic abnormalities affecting the proteins responsible for blood coagulation are afflicted with a disease (hemophilia) in which the blood fails to clot normally, subjecting the individual to the danger of uncontrolled bleeding. For many years, this condition has been treated by administering concentrates of the missing or defective proteins. Many clotting factors are synthesized in the liver so that victims of liver disease are also in need of augmentation of their clotting factors. Additionally, there are other important medical uses for clotting-related factors including the use of fibrin to produce "fibrin sealant" or "fibrin glue".

While some of the clotting factors are currently produced through biotechnology, at this time there is still no cost effective method of artificially manufacturing all of these proteins or these proteins in sufficient quantities. Further, the "artificially produced" factors made by recombinant and related technologies tend to be more expensive. Many of the "minor" factors are not yet (and may never be) available from biotechnology sources and so must be purified from donated human blood. Also, there is often a synergy between factors whereby a single administered recombinant factor is not nearly as effective as a natural mixed fraction produced from fractionated blood. There is also a special problem in Third World countries where the biotechnology products are generally either not available or not affordable. Therefore, much of the supply of anti-hemophilia factor (AHF, also known as Factor VIII), and other blood clotting factors are prepared from pooled human plasma. A hemophiliac requires treatment for a whole lifetime. Victims of liver disease and other users of clotting factors may also require prolonged treatment. Therefore, these patients are exposed to blood products produced from the blood of a large number of donors.

The presence of AIDS (Acquired Immuno Deficiency Syndrome) virus or HIV in the blood supply means that hemophiliacs and other users of clotting factors have become infected with this terrible disease. Although tests to screen out AIDS-tainted blood have been improved, some infected blood does slip by. Even if the AIDS problem is solved, the danger of other blood-borne diseases, such as the various types of hepatitis and other, as yet unknown, infectious agents, makes it desirable to reduce or eliminate virus and other disease organisms from plasma used to prepare clotting factors. One way of achieving this goal is to replace pooled plasma products with products from a single donor products since with pooled products "one bad apple spoils the entire barrel". However, even with the use of clotting factors derived from a single donor, there is still danger. Even though tests may show the donor is free of known disease, the donor may be incubating a disease that will later show up on the tests, or the donor may harbor a yet unknown disease or a yet unknown strain of a known disease. These dangers have been lessened by use of plasma pre-treatments that inactivate disease organisms. Unfortunately, the best commonly used treatments either do not inactivate all types of disease organisms or damage the labile clotting factors during the process of inactivating disease organisms.

The basic methods for preparing clotting factor concentrates from blood have not changed greatly over the last few decades. Generally, a concentrate of clotting factors is derived from pooled plasma by a cryoprecipitation step. The plasma is frozen and then thawed. During the freezing process certain proteins precipitate to form a "cryoprecipitate." Various additives such as ethanol and/or polyethylene glycol are usually added to enhance the efficiency of the cryoprecipitation step. Following cryoprecipitation, the partially purified factors may be further purified by additional precipitation steps or by chromatographic methods, and most recently by methods using monoclonal antibodies. For additional information on the basic techniques of clotting factor purification and the history of the development of these methods, the reader is directed to U.S. Pat. Nos. 3,560,475, 3,631,018, 3,682,881, 4,069,216, and 4,305,871 and 5,770,704 by the present inventor, the contents of which are incorporated herein by reference and the references cited therein.

SUMMARY OF THE INVENTION

It is an object of the present invention to enhance the yield and purity of cryoprecipitate;

It is a further object of the present invention to inactivate and/or enhance the inactivation of disease organisms within plasma at the same time that cryoprecipitate production is enhanced and the cryoprecipitate is further purified.

It is a further object of the present invention to inhibit the activation or denaturation of blood components, including blood cells and plasma proteins, and/or to remove these activated or denatured components, thereby improving the safety and efficacy of the end product.

It is an additional object of the present invention to provide an improved method for blood fractionation.

Derivatives of simple carboxylic acids, particularly trisodium citrate and other citric acid salts (hereinafter "citrate") are shown to be unexpectedly effective agents for enhancing the production of blood clotting factors. It is believed that other small carboxylic acids, isocitric acid in particular, may show similar properties. However, to date most of the tests have been made with citric acid and its salts. Addition of citrate to plasma, especially at concentrations between 2 and 10% by weight, does not appreciably denature labile proteins. However, in this concentration range citrate is effective in inactivating or inhibiting a variety of pathogenic microorganisms. Further, the added citrate potentiates or enhances the killing of microorganisms by heat treatment. That is, heating of the material to relatively low temperatures (i.e., usually above about 45° C.) which do not denature proteins enhances the killing of microorganisms in the presence of citrate. Most significantly, added citrate causes a dramatic increase in the weight of cryoprecipitate that can be produced from plasma by the usual procedures. The majority of significant clotting factors are greatly concentrated in the resulting cryoprecipitate. The supernatant contains little if any of these clotting factors. It is apparent that increasing the amount of citrate in blood bags so that the final concentration will be at least 2% by weight results in plasma that can be used to produce improved platelet concentrates and enriched cryoprecipitate. The added citrate can help eliminate or suppress contaminating microorganisms and can itself be removed later by ion exchange or similar methods well known in the art.

Another aspect of the invention is the use of citrate to enhance the yield and purity of cryoprecipitate. Not only does added citrate increase the amount of cryoprecipitate; it simplifies the process by decreasing the requirement for freezing. Furthermore, added citrate can inhibit the activation or denaturation of blood components including blood cells and plasma proteins and/or facilitate the removal of the activated or denatured components and improves the safety and efficacy of end products.

According to the invention there is provided a method for reducing transfusion-associated disease and adverse effects in plasma and for enhancing the purity and safety of multiple derivative components of blood including blood cells and plasma. In this method, there is the step of adding at least about 2% by weight of carboxylic acid salt or equivalent weight of carboxylic acid to the blood or plasma.

Moreover, the invention is directed to enhancing the production of other derivative blood components including blood cells and plasma proteins.

The invention includes reducing transfusion-associated disease and adverse effects in plasma and for enhancing the purity and safety of multiple derivative components of blood including blood cells and plasma from plasma. The derivatives comprises at least one product from the group of Enriched Cryoprecipitate, Cryo-Depleted Plasma, Fibrinogen, Fibrin Glue or Sealant, vWF (von Wilidebrand's factor), Fibronectin, Factor VIII, Prothrombin Complex, a Serpine, Albumin, and a Globulin (such as γ-Globulin) from plasma. At least 2% by weight of a salt of citric acid (or equivalent weight of citric acid with concomitant control of pH) is added to the plasma. The plasma may be collected into a blood bag containing the carboxylic acid or the carboxylic acid salt. This blood bag can be different from a bag or container used to collect whole blood. Alternatively or additionally, an amount of additional carboxylic acid or the salt thereof may be added directly to the bag used to collect the whole blood.

In a further preferred form of the invention, citrate is used appropriately in the collection of blood, in the processing and transfer of blood and in a separation of discrete blood components. Citrate is used in increased, namely, additional quantities over the level traditionally employed for anticoagulation in one or other collection or processing bag.

DETAILED DESCRIPTION OF THE INVENTION

Figure 1:
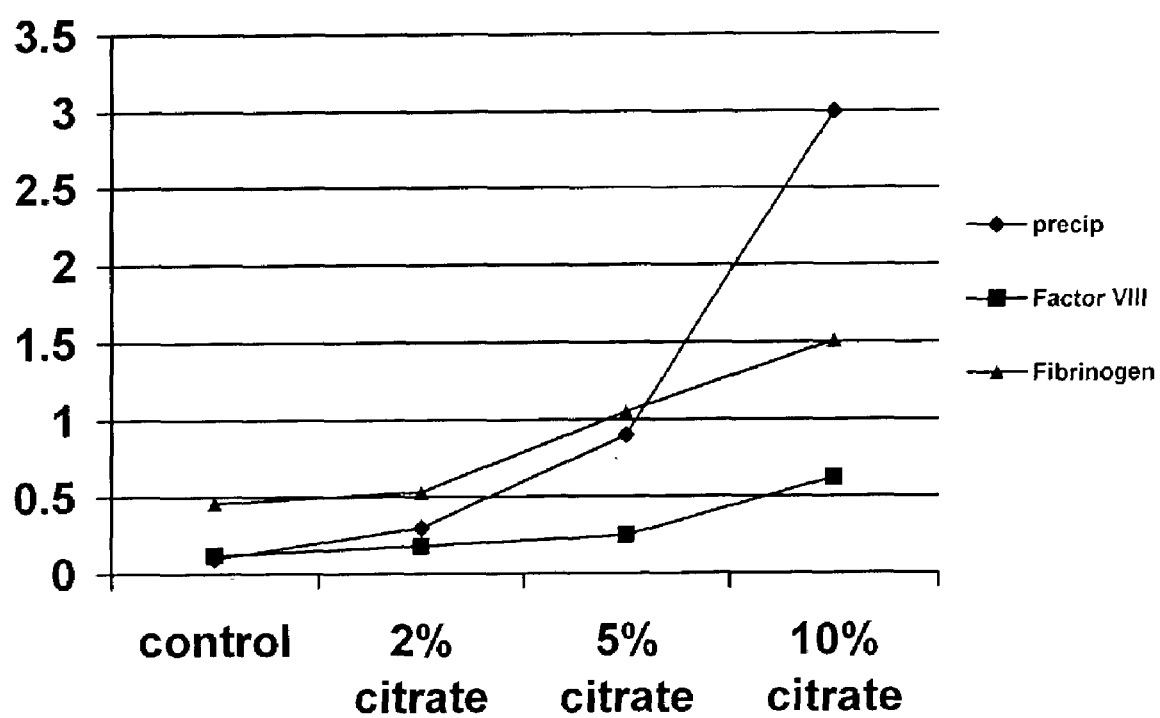
FIG. 1 is a graphic representation of the improvement in cryoprecipitate yield resulting from the present invention.

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide enhanced production of plasma proteins along with inactivation of blood borne disease organisms.

The traditional method for producing clotting factors, as well as many of the presently used methods, operate because many plasma proteins responsible for clotting precipitate (i.e., form cryoprecipitate) from solution at low temperatures when they are sufficiently concentrated. When a protein solution is frozen, ice crystals form and protein molecules, which are excluded from the crystals become increasingly concentrated. Cooling or freezing the water also lowers the chemical activity of the water. Depending on the particular proteins, the proteins may actually fall out of solution, i.e., form a precipitate, if the protein more readily interacts with itself or with other proteins than with water. When the chemical activity of water is lowered such precipitation is favored. This process may denature the proteins (make them irreversibly insoluble), so it is usual to freeze protein solutions rapidly and to a low temperature (i.e., −20° C. or lower) to minimize the formation of ice crystals and to prevent the growth of those crystals that do form. This is done to limit protein denaturation on ice crystal surfaces. However, even when freezing is carried out with great care, ice crystals may cause "activation" of the prothrombin complex, resulting in spontaneous clot formation after the plasma is thawed.

The first step in the typical procedure for producing plasma cryoprecipitate is to centrifuge whole blood to separate the plasma from the red blood cells. This procedure is well known in the art and is often accomplished in special centrifuges that hold individual blood bags so that the plasma/red cell separation occurs without even opening the blood bag. Following the centrifugation, it is common practice to express the supernatant plasma into a "satellite" blood bag for further processing. Once the plasma is separated from red and white blood cells, the typical procedure is to rapidly freeze the plasma and to then slowly thaw the frozen plasma at about 4° C., during which thawing the clotting factors and other proteins form a cryoprecipitate which can be readily harvested by filtration or centrifugation. This cryoprecipitate is not rendered irreversibly insoluble and can be readily redissolved in a saline buffer, or even water, as is well known in the art.

Cryoprecipitation is generally believed to result when the removal of water from the immediate vicinity of the protein molecules causes the protein molecules to preferentially associate with each other rather than with water. This "removal" of water may represent changes in the solubility of the proteins with changes in temperature (i.e., water becomes less effective at dissolving the proteins). The process may also be accomplished or enhanced by using additives which "tie up" the water and cause it to interact with the proteins to a lesser degree. These additive substances can be any of a number of hydrophilic materials such as ethanol, polyethylene glycol, heparin, Pluronic RTM polyol polymers and various "salts" such as ammonium sulfate or ammonium acetate. The "salting out" of proteins from solution is a classical biochemical procedure. These and other materials used to increase the yield of cryoprecipitate generally operate to decrease the effective activity of water in the mixture. That is, the water molecules preferentially interact with the added hydrophilic material instead of with the proteins. This permits the proteins to interact with each other and, therefore, precipitate from solution. Similarly, lowering the temperature also decreases the activity of water, allowing protein-protein interactions to predominate.

The hydrophilic additives just mentioned have the advantage of being relatively inexpensive and easy to use. However, their use usually necessitates additional washing steps to ensure that the additives are not carried over into the final product. Some additives may also damage or denature the labile clotting factors one is seeking to purify. The present inventor has discovered that one of the agents frequently used as an anticoagulant in blood fractionation unexpectedly serves to enhance cryoprecipitate formation. Citrate (trisodium citrate or similar salts as well as derivatives of other low molecular weight carboxylic acids such as isocitric acid) has unusually favorable properties when used in blood fractionation procedures at levels significantly higher than those traditionally used as an anticoagulant. Citrate is a fairly effective chelator of calcium ions. By effectively lowering the calcium ion level, citrate inhibits a considerable variety of blood clotting pathways which depend on the presence of calcium ions. However, citrate has not been employed as an agent to enhance the preparation of cryoprecipitate proteins from plasma and other blood fractions.

The following table shows the enhanced production of cryoprecipitate caused by increasing the level of trisodium citrate in plasma. As the citrate is increased, the weight of recovered cryoprecipitate is increase. When the cryoprecipitate is redissolved in a fixed quantity of buffer or water, the increasing amount of cryoprecipitate yields increasing amounts of Factor VIII and fibrinogen as compared to the original plasma. The precise reason for this increase in yield is not known. However, it seems reasonable to speculate that one action of citrate may be to inhibit the activation of clotting factors. Since many of these factors act as proteases when activated, activation naturally digests clotting proteins thus reducing the yield of these proteins. However, lack of inactivation does not seem sufficient to account for the entire increase in cryoprecipitate yield.

| Treatment | Cryoprecipitate | Factor VIII | Fibrinogen |
| --- | --- | --- | --- |
| control | 0.1 g | 120% | 46 mg/dl |
| 2% citrate | 0.3 g | 180% | 53 mg/dl |
| 5% citrate | 0.9 g | 247% | 105 mg/dl |
| 10% citrate | 3.0 g | 622% | 152 mg/dl |

These data are graphically represented in FIG. 1. These results indicate that as the citrate concentration is increased the amount of recovered clotting factors increases linearly. However, at the highest concentration of citrate it would appear that there might be an increase in the precipitation of other proteins. It may be possible to adjust the citrate concentration to favor the precipitation of different proteins. Tests have shown that besides more than 95% of the Factor VIII and Fibrinogen, virtually all of the Fibronectin and the von Willdebrand's factor become concentrated in the citrate-enhanced cryoprecipitate. Additional experiments have been undertaken to determine if metalloproteins or other factors are preferentially concentrated in the citrate cryoprecipitate. Initial results do not show any other proteins as strongly concentrated as those already mentioned. However, there is some indication that ceruloplasmin and total T3 are somewhat concentrated in the cryoprecipitate.

On the surface, one might not expect citrate to be more effective than any hydrophilic salt. In terms of salting proteins out of solution, one would expect various agents to operate based on their colligative properties. That is, one might expect equimolar concentrations of various agents to behave similarly. This does not appear to be the case with citrate and cryoprecipitate formation.

The following quantities of either salt (NaCl) or citrate (trisodium citrate) were added to 40 ml aliquots of fresh human plasma. After thorough mixing the samples were frozen overnight at −70° C. and then completely thawed at 4° C. The samples were then centrifuged at 4000 RPM for 20 min to harvest the cryoprecipitate. An attempt was made to match the effective sodium concentration between the sodium chloride and sodium citrate on the basis that each molecule of trisodium citrate would provide three sodium ions whereas each molecule of sodium chloride would provide only a single sodium ion. This attempt at compensation was inaccurate because the matching should be done on a molar rather than a percent basis. However, this failed experiment points out the incredible superiority of sodium citrate over sodium chloride for producing cryoprecipitate. In the following table the citrate (trisodium citrate) or table salt (sodium chloride) are shown, first as weight percentages and then as molarities. The third column shows the effective osmotic effect of the solutions, which is two times higher on a molar basis for citrate than for sodium chloride. This is because each molecule of sodium chloride releases only two particles (one sodium ion and one chloride ion) whereas each molecule of trisodium citrate releases four particles (three sodium ions and one citrate ion). Because the molecular weight of trisodium citrate is almost 5 times greater than that of salt to get equal osmotic effects one must use about 2.5× (on a weight basis) as much trisodium citrate as sodium chloride. That is, for an accurate matching more citrate rather than more salt should have been used.

| Weight % | Molarity | Osmotic Effect | Cryoprecipitate |
| --- | --- | --- | --- |
| Control | — | — | 0.18 g |
| 2% citrate | 0.07 | 0.28 | 0.52 g |
| 5% citrate | 0.17 | 0.68 | 1.3 g |
| 10% citrate | 0.34 | 1.36 | 3.6 g |
| 6% sodium chloride | 1.02 | 2.04 | 0.12 g |
| 15% sodium chloride | 2.56 | 5.13 | 0.14 g |
| 30% sodium chloride | 5.13 | 10.26 | 0.15 g |

These results show that the effect of citrate on cryoprecipitate production is not strongly related to the colligative or osmotic properties of the citrate. Sodium chloride seems not to enhance cryoprecipitate formation. Only at osmotic levels that are greatly above those of the maximal citrate concentration, cryoprecipitate formation begins to approach that of the control plasma. Further, the resulting cryoprecipitate does not appear as pure (that is, larger amounts of other non-clotting proteins are included).

Following the experiment, the supernatants and the original plasma (control) were sent to a clinical chemistry laboratory to determine the presence of various blood proteins including clotting factors. These results are shown in the following table.

| Weight % | Fibrinogen (mg/dl) | Factor VIII (%) | Albumin (g/dl) |
|---|---|---|---|
| Control | 287 | 24 | 3.2 |
| 2% citrate | 216 | 6 | 3.1 |
| 5% citrate | 114 | <3 | 3.2 g |
| 10% citrate | <40 | <3 | 3.2 g |
| 6% NaCl | 298 | 30 | 3.1 g |
| 15% NaCl | 229 | 24 | 3.0 g |
| 30% NaCl | 97 | 9 | 2.9 g |

As the amount of citrate is increased the levels of fibrinogen and Factor VIII in the supernatant decrease dramatically. At the same time, the level of albumin (the major plasma protein) is essentially unaffected. In other words, most of the clotting factors precipitate and are found in the cryoprecipitate, but little or no albumin precipitates. In the case of sodium chloride, equimolar concentrations are much less effective at precipitating the clotting factors. One has to go up to 30% sodium chloride to see a significant precipitation of the clotting factors. However, at this level the albumin also begins to precipitate. Citrate is far more effective at selectively precipitating the clotting factors.

Further insight into the citrate effect is gleaned by analyzing the distribution of citrate in a typical cryoprecipitate experiment. For this experiment, one unit (about 200 ml) of plasma was brought to 10% wt/vol. trisodium citrate. In all experiments pH measurements showed that natural buffering of the plasma prevented significant changes in pH. This citrate-treated plasma was frozen and cryoprecipitate was collected in the usual manner. As an aside, in producing citrate cryoprecipitate it is preferred to add the citrate prior to freezing, but good results are achieved by adding the citrate during the thawing process. As will be demonstrated below, actual freezing is not even necessary.

The volume of cryoprecipitate formed from the unit of plasma was approximately 20 ml—that is, 10% of the total volume. Surprisingly, an analysis of the cryoprecipitate and the supernatant plasma showed that about 12 g (60%) of the citrate was concentrated in the cryoprecipitate with only 30% being left in the supernatant. This indicates that there is a strong interaction between the cryoprecipitate proteins and the citrate. The proteins become "citrified" or "citrated" upon incubation with elevated concentrations of citrate. Further, while normal cryoprecipitate can be redissolved in room temperature water or buffer, citrated cryoprecipitate is relatively insoluble in room temperature water. It is soluble, however, in room temperature saline buffer and most soluble when the buffer contains citrate. One way of explaining these phenomena is to assume that the multiple negative charges on the citrate molecule are interacting with positive charges on the cryoprecipitate proteins to cross-link them. Added citrate "satisfies" these positive charges so that cross-linking is abolished. Because of the concentration of clotting proteins into the cryoprecipitate, it is tempting to theorize that all of the clotting proteins share some sort of positive charge motif that interacts with the citrate molecules. It may be that other proteins will also become "citrified" if incubated with a sufficiently high concentration of citrate.

In summary, compared to "normal" cryoprecipitate citrated cryoprecipitate contains essentially all of the Fibrinogen, Fibronectin, Factor VIII and von Willdebrand's factor found in a treated aliquot of plasma. The citrated cryoprecipitate may also contain other minor factors (like Factor XIII) not yet assayed in these experiments. What may be significant is what the citrated cryoprecipitate does not contain. It has significantly less of albumin, globulins and other minor proteins than "normal" cryoprecipitate. Experiments are on going to characterize these differences.

Although citrate appears to influence strongly the precipitation of the clotting factors, it does not appear to denature these proteins. Citrate at 2% by weight was added to an aliquot of plasma that was stored at room temperature for six days. Clotting factors and platelets were counted at the beginning and the end of the time period. As compared to control plasma, the addition of citrate did not appear to harm the clotting factors. There is actually some suggestion that the citrate may actually help preserve platelets. This would be consistent with the hypothesis that citrate inhibits some of the proteases.

2% Citrate Plasma

| Measurement | Day 1 | Day 6 |
|---|---|---|
| Fibrinogen (mg/dl) | 243 | 239 |
| Factor II (%) | 104 | 91 |
| Factor V | 49 | 22 |
| Factor VII (%) | 81 | 72 |
| Factor VIII (%) | 103 | 92 |
| Factor IX (%) | 106 | 95 |
| Factor X (%) | 92 | 97 |
| Platelets ($10^3/10^{-6}$L) | 311 | 239 |
| PT (sec) | 14.1 | 16.2 |
| PTT (sec) | 31.4 | 47.9 |

Control Plasma

| Measurement | Day 1 | Day 6 |
|---|---|---|
| Fibrinogen (mg/dl) | 241 | 239 |
| Factor II (%) | 103 | 93 |
| Factor V | 58 | 25 |
| Factor VII (%) | 86 | 69 |
| Factor VIII (%) | 100 | 89 |
| Factor IX (%) | 106 | 92 |
| Factor X (%) | 93 | 85 |
| Platelets ($\times 10^3/10^{-6}$L) | 317 | 192 |
| PT (sec) | 13.7 | 19.5 |
| PTT (sec) | 32.5 | 50.2 |

As was mentioned above, it has been found that addition of citrate to frozen plasma during the freezing process appears to be as effective at increasing the amount of cryoprecipitate as adding the citrate prior to freezing. Of course, in most cases it is more convenient to add the citrate to the blood bags prior to collection or expressing the plasma, or perhaps during the pooling of plasma prior to freezing. However, there are cases where pooled plasma is stored and shipped in the frozen state so that it is a significant advantage that the new enhanced citrate process can be used with such plasma even if the plasma was frozen before the new process was even invented.

In investigating this phenomenon it was discovered that freezing is not even necessary. In the experiment 40 ml aliquots of human plasma were brought to 10% wt/v trisodium citrate by the addition of 10 ml aliquots of a 50% wt/v trisodium citrate stock solution. After mixing the aliquots were stored for 24 hours at 4° C. At the end of this time a large white precipitate had formed in each sample. The samples were centrifuged at 1,500×g for 10 minutes in a refrigerated centrifuge to pellet the precipitate. The supernatant was carefully poured off, and each pellet was redissolved in 10 ml of 0.9% NaCl. A check of pH showed that it remained in the normal physiological range. Calcium chloride was added to the solutions to overcome the citrate, and each solution was sent to an independent laboratory for determination of Factor VIII and fibrinogen. The results are shown in the following Table

| Aliquot | Pellet | | Supernatant | |
|---|---|---|---|---|
| 4° C. | Factor VIII | Fibrinogen | Factor VIII | Fibrinogen |
| 1 | 422% | 1,205 mg/dl | not detected | not detected |
| 2 | 408% | 1,100 mg/dl | not detected | not detected |
| 3 | 436% | 1.010 mg/dl | not detected | not detected |
| 4 | 389% | 1,196 mg/dl | not detected | not detected |
| 5 | 401% | 1,301 mg/dl | not detected | not detected |

These results show that essentially all of the Fibrinogen and Factor VIII ended up in the pellet. Since the pellet from 40 ml of plasma was resuspended in 10 ml of saline one would expect a four-fold increase if all of these proteins were in the pellet. This is essentially what the tests show within their margin of error. Similarly, the Fibrinogen readings are about four times higher than normal. The small amount of Factor VIII and Fibrinogen in remaining in the supernatant is below the detection limits of the tests. This finding shows that it is possible to dispense with the cumbersome freezing and thawing steps altogether. With this method "cryo" takes on it's preferred etymological meaning of "icy cold" rather than frozen.

In fact, it appears that even icy cold is not strictly necessary. The following table shows the results of an experiment carried out exactly like the previous experiment except that the aliquots were allowed to rest for 24 hours at room temperature (approximately 21° C.) prior to centrifugation. The results show that the separation was almost as good as at the lower temperature. Further experimentation is necessary to determine whether 4° C. is a "magic value" or if some temperature lower than 21° C. but higher than 4° C. will produce optimum results. Also, it is possible that a longer time at 21° C. will produce improved results. In any case, the difference between the results at 21° C. and 4° C. is small. Either of these temperatures with citrate produces yields superior to current frozen cryoprecipitates without additional citrate. It would appear that simple incubation with elevated levels of citrate allows binding of the citrate or "citrification" of the proteins which results in precipitation. When the citrate level is reduced (as in resuspension in saline) the proteins readily go back into solution—indicating that they are not damaged by the "citrifying" process.

| Aliquot | Pellet | | Supernatant | |
|---|---|---|---|---|
| 21° C. | Factor VIII | Fibrinogen | Factor VIII | Fibrinogen |
| 1 | 386% | 1,100 mg/dl | not detected | not detected |
| 2 | 411% | 992 mg/dl | not detected | not detected |

Significantly, bacteriology experiments showed that 2% trisodium citrate strongly inhibits growth of *Escherichia coli* and completely inhibits the growth of *Staphylococcus epidermidis*. Growth of bacteria (primarily skin bacteria from inadequate surface disinfection) in platelet concentrates significantly lowers the useable life of platelet-rich solutions: Addition of citrate inhibits bacterial growth thereby potentially extending the life of such concentrates. As has been demonstrated above, addition of citrate does not damage the plasma constituents and actually significantly enhances the production of cryoprecipitate. Therefore, it is proposed to significantly increase the level of citrate in blood collection bags from the 0.4% currently used for anticoagulation to at least 2% trisodium citrate by weight. This level would inhibit or kill many contaminating microorganisms and would render the plasma more suitable for production of cryoprecipitate. It is also a simple matter to add trisodium citrate just before cryoprecipitate production where levels beyond 2% are needed.

Added citrate appears to enhance the susceptibility of microorganisms to a variety of "disinfecting agents" including heat. In one experiment 2%, sodium citrate was added to a typical bacterial growth broth. Twenty-five ml aliquots of the broth were spiked with $1 \times 10^4$ organisms of either *Escherichia coli* or *Staphylococcus epidermidis*. Samples of the broth were brought to 2% by weight trisodium citrate and then subjected to "pasteurization" at 65° C. for either 5 or 10 min. after which the samples were plated on growth media and incubated. The 10 min citrate treatment caused total destruction of the bacteria. At 10 min the control bacteria were essentially unaffected. However, the 5 min treatment citrate did not kill all of the *E. coli* bacteria (approximately a 3-log kill). *Staphylococcus epidermidis* was more sensitive and was completely killed in the presence of citrate. Addition of citrate clearly enhances the ability of heat to kill microorganisms. Further, added citrate appears to stabilize labile proteins against heat denaturation. These results indicate that addition of increased citrate makes possible effective heat treatment of the plasma.

A problem with platelet concentrates and with plasma is the growth over time of bacteria that are originally present in very low numbers. Some of the contaminating bacteria apparently come from the skin surface when the blood is obtained by venipuncture. Further, there is growing evidence that blood is not completely aseptic. That is, there are normally a small number of bacteria circulating in the human bloodstream. Normal immunity prevents the overgrowth of these bacteria. To simulate this situation 10 ml samples of human plasma were inoculated at very low levels (10 organisms per ml) with the bacteria listed in the following table. Either normal plasma (N) or plasma with 2% by weight of citrate (C) was employed. The samples were incubated at room temperature for seven days with a sample plated on growth agar at each time point. Three different human plasmas were used, but all produced identical results. In the table "ng"="no growth" while "+" indicates some bacterial growth and "++" indicates more extensive growth.

| In-ocu-lum | Day 1 | | Day 2 | | Day 3 | | Day 4 | | Day 5 | | Day 6 | | Day 7 | |
|---|---|---|---|---|---|---|---|---|---|---|---|---|---|---|
| | N | C | N | C | N | C | N | C | N | C | N | C | N | C |
| a) | ng | ng | ng | ng | ng | ng | ng | ng | ng | ng | + | ng | ++ | ng |
| b) | ng | ng | ng | ng | ng | ng | ng | ng | ng | ng | + | ng | ++ | ng |
| d) | ng | ng | ng | ng | ng | ng | ng | ng | ng | ng | + | ng | ++ | ng |
| e) | ng | ng | ng | ng | ng | ng | ng | ng | ng | ng | + | ng | + | ng |
| f) | ng | ng | ng | ng | ng | ng | ng | ng | ng | ng | + | ng | + | ng |
| g) | ng | ng | ng | ng | ng | ng | ng | ng | ng | ng | ng | ng | ng | ng | a) *Escherichia coli*
b) *Klebsiella pneumoniae*
c) *Staphylococcus epidermidis*
d) *Staphylococcus aureus*
e) *Pseudomonas fluorescens*
f) *Yersinia enterocolitica*
g) *Serratia marcescens*

At days six and seven, the normal plasma showed growth of all of the inoculated bacteria species except for *Serratia*. On the other hand, none of the plasma samples containing citrate demonstrated any bacterial growth. This indicates that 2% by weight citrate is able to inhibit strongly the growth of a wide range of bacteria. Combining these results with the favorable platelet results demonstrates that addition of 2% or more citrate to platelet concentrates can preserve the concentrates against bacterial growth without damaging the platelets. If there is any concern about excess citrate in the platelets, it can be readily removed by treatment with an anion exchange resin or similar material.

It was suspected that the failure to observe *Serratia* was due to the slow growth rate of this organism. Therefore, the experiment was repeated using *Serratia marcescens* and *Staphylococcus epidermidis* to inoculate plasma samples at the level of 100 organisms per ml. In this case the one-day time point for *Serratia* showed 92 colonies while that for *Staphylococcus* showed 101 colonies for the normal plasma. Thus, no growth was observed in either case for the citrate-containing plasma.

The precise mechanism by which citrate and similar molecules act is not know. Multiple carboxyl groups appear important particularly in the case of cryoprecipitate. Oxalic and lactic acids are less effective. It seems possible that some type of charge interaction favors the precipitation of the clotting factors. As mentioned above, there appears to be good data supporting the hypothesis that citrate preferentially cross-links the cryoprecipitate proteins. While chelating ability is clearly important for the well known anticoagulation effects of citrate, chelation may not be central to the present invention as isocitrate is believed to be a poorer chelating agent than citrate. It may also be that the participation of many of the effective molecules in the tricarboxylic acid cycle may also be related to their effects—particularly those on bacterial growth. That is, it seems likely that the cryoprecipitate phenomenon and the bacterial growth phenomenon have separate explanations.

The invention has mainly been described with regard to cryoprecipitate. There are other characteristics, and blood components, and products that form the subject of the invention. These are illustrated in the attached FIG. 2 that shows a Fractionation Scheme, and different blood components and plasma proteins, which are obtained from the system and to which the citrate technology is applied. The starting point is collected blood—here a bag of CPDA (citrate-phosphate-dextrose-adenine) treated blood. The extra citrate could be added to this first bag or could be added, for instance, at the stage of the second empty bag with that bag containing citrate at an effective concentration of greater than about 2% to about 10% by weight or by volume trisodium citrate. As mentioned above, the citrate can even be added at the frees/thaw step. Because of this further addition of citrate, different new products are obtained.

Figure 2:
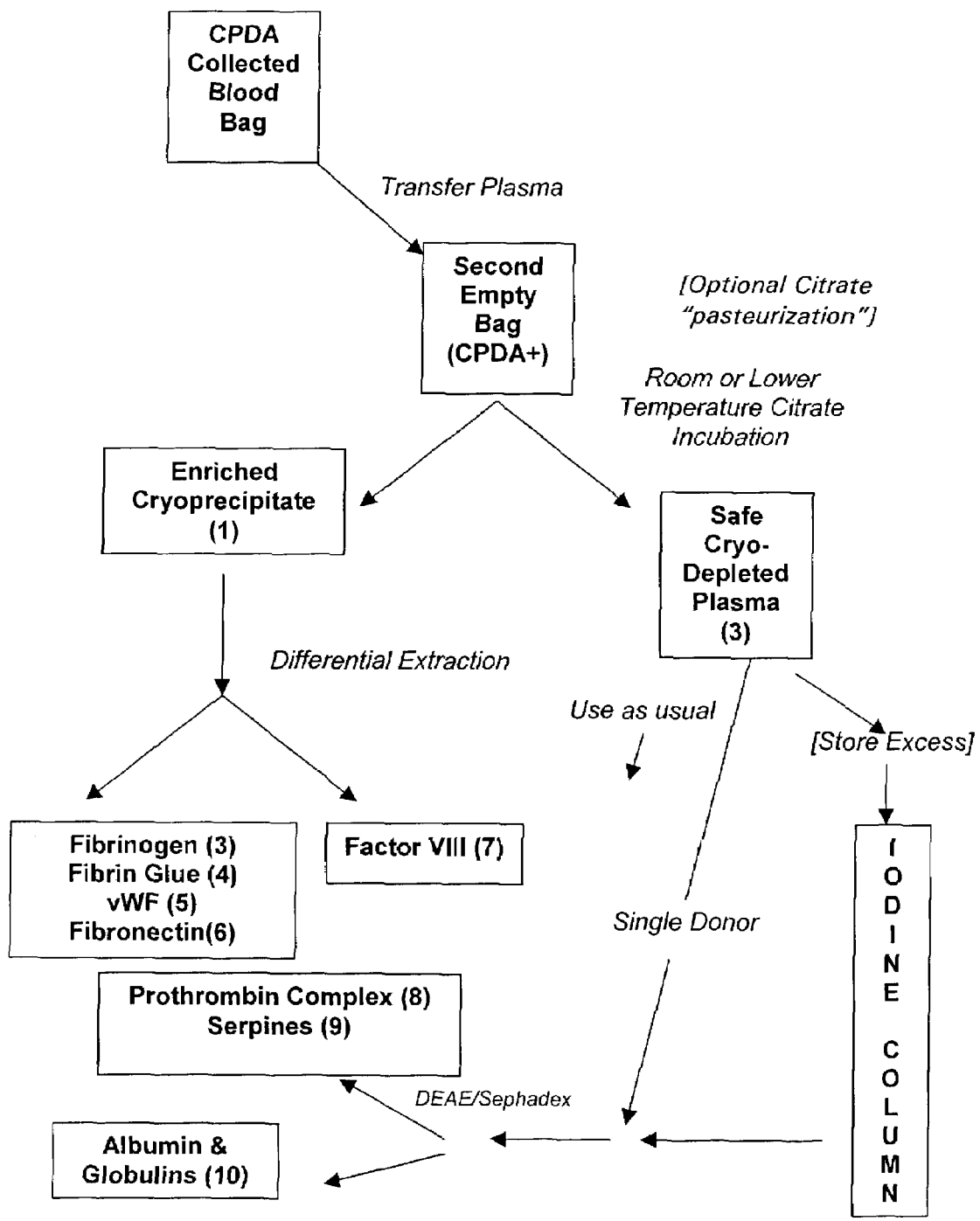
FIG. 2 is a representation of the blood and plasma fractionation scheme using the invention.

This citrate-related process has the following features that relate to FIG. 2:

1. The products and processes starting from the Second Empty Bag onwards show improvements in purity and safety over normally fractionated plasma. The enriched cryoprecipitate 1 is at a higher yield than in the prior art. This means that collected blood can be more efficiently used and the amount of blood wasted as "discard fractions" reduced. The enriched cryoprecipitate 1 has fewer "contaminating" extraneous serum proteins as compared to "normal" cryoprecipitate. If crude fibrin glue 4 is produced directly from enriched cryoprecipitate by addition of thrombin or prothrombin complex (Factors II, VII, IX, and X), the resulting glue is superior in strength to crude fibrin glue produced in the same manner from "normal cryoprecipitate." It compares favorably, and may actually be superior to, highly refined fibrin glue. The processing is simpler because freezing can be avoided and "cryo" can be produced at lowered or at room temperature. In this specification "cryoprecipitate" can mean a protein precipitate produced with no or little cooling. The term "cryoprecipitate" is retained because such a precipitate contains components (namely Factor VIII, fibrinogen, and other clotting factors) found in cryoprecipitate produced in the normal manner by freezing the blood plasma.

The product is safer because citrate inhibits bacterial growth and because citrate can facilitate a "pasteurization" step to further destroy pathogens. Further, because of the higher yield of enriched cryoprecipitate, and greater strength of the crude fibrin glue autologous fibrin glue becomes much more feasible. Autologous products are inherently safer because they eliminate the danger of transfusion transmitted diseases. Further, because of the much greater yield of fibrinogen with enriched cryoprecipitate, it is feasible to produce "refined" fibrin glue or sealant which is primarily pure fibrinogen plus thrombin (added during application) although Factor VIII and other ingredients may be included.

The cryo-depleted plasma 3 is safer for the above mentioned reasons. It is also inherently safer because it contains far less fibrinogen than normally processed plasma. This means it is virtually impossible for this material to develop microclots due to activation of the prothrombin complex—such microclots can cause intravascular coagulation and related transfusion problems. Also, the elevated citrate level reduces the likelihood of activation of prothrombin complex. A second bag with the increased carboxylic acid and/or citrate derivative (or other use of higher levels of carboxylic acid/citrate) is a feature which prior to the present invention has never been part of a blood fractionation process or part of the production of blood components for clinical use. There are significant advantages to using increased citrate (or related carboxylic acids).

2. Fibrinogen 3, Fibrin Glue 4, von Willdebrand's factor 5, Fibronectin 6 and Factor VIII 7 can be produced by standard chromatographic methods, but use of differential extraction simplifies the process. As mentioned above, the enriched citrate cryoprecipitate 1 is mostly insoluble in water. It is soluble in normal saline and very soluble as saline to which citrate is added. Therefore, extraction with buffers having different amounts of citrate or other salts results in preferential solubility of the different products.

3. Products 8, 9 & 10 can be produced from Single Donor or from Pooled Plasma (preferably in combination with Iodine disinfection—as detailed, for example, in U.S. Pat. No. 6,045,787, which is incorporated herein by reference).

4. It is also possible to use iodine disinfection before the cryoprecipitate step. A co-pending application demonstrates that citrate enhances the iodine treatment. However, the columns used in the referenced patent remove citrate. Therefore, after Iodine disinfection, additional citrate can be added at the second blood empty bag step but before the formation of cryoprecipitate.

Albumin & Globulins (product 10) may be further fractionated to yield separate albumin and gamma globulin. Generally, well-known fractionation techniques can be used. Anion exchange (DEAE) is used to purify prothrombin complex. DEAE/sephadex can be used in a single donor process both to purify prothrombin and to dehydrate. Serpines 9 are purified by standard methods. Yields are improved because of the protease inhibiting properties of the added citrate. Again, these products are safer because of the citrate, because of the iodine step, because single donor products can be readily prepared and because pasteurization is facilitated.

The invention covers the process and products obtained by the process. The following claims are thus to be understood to include what is specifically illustrated and described above, what can be obviously substituted and also what incorporates the essential idea of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A method for reducing bacterial growth in platelet concentrates comprising the steps of adding at least 2% by weight of citric acid or citric acid salt to a platelet concentrate.

2. The method of claim 1, wherein a trisodium salt of citric acid is added to the platelet concentrate.

3. The method of claim 1 further comprising the step of heating the platelet concentrate above 45° C. following addition of the citric acid or the citric acid salt.

4. The method of claim 1 further comprising the step of removing the citric acid from the platelet concentrate by means of ion exchange chromatography.

5. A method for reducing bacterial growth in blood plasma and fractionating the plasma without freezing comprising the steps of adding at least 2% by weight citric acid or citric acid salt to blood or blood plasma; forming a "cryoprecipitate" at a temperature above freezing and without freezing the blood plasma; and removing the carboxylic acid or the citric acid salt from the blood plasma by means of ion exchange chromatography.

6. The method of claim 5, wherein the at least about 2% citric acid or citric acid salt is trisodium citrate.

7. The method of claim 5, wherein the blood plasma is placed into a blood bag containing the at least about 2% by weight citric acid or citric acid salt.

8. The method of claim 7, wherein the blood bag is different from a bag or container used to collect whole blood from a patient.

9. A method for reducing bacterial growth in plasma and for fractionating plasma without freezing comprising the steps of:

adding at least about 2% by weight of citric acid or citric acid salt to blood plasma;

incubating the blood plasma at a temperature above freezing to produce an enriched cryoprecipitate and cryo-depleted plasma;

separating the enriched cryoprecipitate from the cryo-depleted plasma; and fractionating the enriched cryoprecipitate to produce at least one of fibrinogen, von Willdebrand's factor, fibronectin and Factor VIII.

10. The method of claim 9, wherein the fibrinogen is used to produce fibrin glue.

11. The method of claim 10, wherein the fibrin glue further comprises at least one of prothrombin complex and thrombin.

12. The method of claim 9, wherein the fractionation step includes differential extraction.

13. A method for reducing bacterial growth in plasma and for fractionating plasma without freezing comprising the steps of:

adding at least 2% by weight of citric acid or citric acid salt to blood plasma;

incubating the blood plasma at a temperature above freezing to produce an enriched cryoprecipitate and cryo-depleted plasma;

separating the enriched cryoprecipitate from the cryo-depleted plasma; and producing fibrin glue from the cryoprecipitate.

14. The method of claim 13, wherein the fibrin glue further comprises at least one of prothrombin complex and thrombin.

15. A method for reducing bacterial growth in plasma and for producing multiple derivative components of blood through fractionating plasma without freezing comprising the steps of:

adding at least 2% by weight of citric acid or citric acid salt to blood plasma;

incubating the blood plasma at a temperature above freezing to produce an enriched cryoprecipitate and cryo-depleted plasma;

separating the enriched cryoprecipitate from the cryo-depleted plasma; and fractionating the cryo-depleted plasma to produce at least one of prothrombin complex, serpine, albumin and globulin.

16. The method of claim 15, wherein the plasma is subjected to an iodine disinfection step.

17. The method of claim 15, wherein the citric acid salt is trisodium citrate.

18. The method of claim 15, further comprising the step of heating the plasma above 45° C. following addition of the citric acid or citric acid salt.

19. The method of claim 15, further comprising the step of removing the citric acid or the citric acid salt by means of ion exchange chromatography.

20. The method of claim 15, wherein the plasma is placed into a blood bag containing the citric acid or the citric acid salt.

21. The method of claim 20, wherein the blood bag is different from a bag or container used to collect whole blood from a patient.

22. Plasma fractions produced without freezing by a method of fractionating plasma comprising the steps of:

adding at about 10% by weight of citric acid or citric acid salt to blood plasma;

incubating the blood plasma at a temperature above freezing to produce an enriched cryoprecipitate and cryo-depleted plasma; and producing fractions by separating the enriched cryoprecipitate from the cryo-depleted plasma.

23. The plasma fractions according to claim 22 consisting of enriched cryoprecipitate.

24. The plasma fractions according to claim 22 consisting of cryo-depleted plasma.

* * * * *